US010716478B2

(12) United States Patent
Meer et al.

(10) Patent No.: US 10,716,478 B2
(45) Date of Patent: Jul. 21, 2020

(54) WEARABLE DEVICE HEART MONITOR SYSTEMS

(71) Applicant: Motorola Mobility LLC, Chicago, IL (US)

(72) Inventors: Daniel J. Meer, Chicago, IL (US); Kent Allen Campbell, Chicago, IL (US); Brett Coakley, Chicago, IL (US); Eric J. Dayringer, Chicago, IL (US); Nicholas Alan Fraser, Chicago, IL (US); Thomas E. Gitzinger, Libertyville, IL (US); Jaeshin Kim, Northbrook, IL (US); Michael L. Neau, Kenosha, WI (US); Mitul R. Patel, Lake Zurich, IL (US)

(73) Assignee: Motorola Mobility LLC, Chicago, IL (US)

( * ) Notice: Subject to any disclaimer, the term of this patent is extended or adjusted under 35 U.S.C. 154(b) by 0 days.

(21) Appl. No.: 14/982,850

(22) Filed: Dec. 29, 2015

(65) Prior Publication Data

US 2017/0181644 A1 Jun. 29, 2017

(51) Int. Cl.
*A61B 5/0205* (2006.01)
*A61B 5/024* (2006.01)
(Continued)

(52) U.S. Cl.
CPC .......... *A61B 5/0205* (2013.01); *A61B 5/0245* (2013.01); *A61B 5/0261* (2013.01);
(Continued)

(58) Field of Classification Search
CPC . A61B 5/0531; A61B 5/02438; A61B 5/0245; A61B 5/0261
See application file for complete search history.

(56) References Cited

U.S. PATENT DOCUMENTS 4,120,294 A    10/1978   Wolfe
5,316,008 A *   5/1994   Suga ................... A61B 5/02125
                                                        600/503

(Continued)

FOREIGN PATENT DOCUMENTS

EP             2989965         3/2016
WO     WO-2016161228    10/2016
WO     WO-2017003794     1/2017

OTHER PUBLICATIONS

MIO Energy Pro Users Guide (note: an article is appended showing the priority date of the MIO Energy Pro model device).*

(Continued)

*Primary Examiner* — Lynsey C Eiseman
*Assistant Examiner* — Amanda L Seinberg
(74) *Attorney, Agent, or Firm* — SBMC

(57) ABSTRACT

In embodiments of wearable device heart monitor systems, a wearable device has electrical contacts integrated in a housing base of the wearable device as electrodes designed to contact skin of a user while wearing the wearable device. A housing bezel of the wearable device designed as an additional point of contact on the wearable device. The wearable device includes an electromyography (EMG) system to receive electrical signals from at least two of the electrodes and detect muscular movement of the user. Further, the wearable device includes an electrocardiogram (ECG) system to receive and combine the electrical signals from the electrodes when the user touch contacts the housing bezel while wearing the wearable device to complete an ECG loop between the electrodes and the housing bezel for a heart rate reading of the user.

20 Claims, 7 Drawing Sheets

(51) Int. Cl.
*G06F 3/01* (2006.01)
*A61B 5/0245* (2006.01)
*A61B 5/026* (2006.01)
*A61B 5/0488* (2006.01)
*A61B 5/053* (2006.01)
*A61B 5/00* (2006.01)
*A61B 5/04* (2006.01)
*A61B 5/0404* (2006.01)
*A61B 5/0408* (2006.01)
*A61B 5/0428* (2006.01)
*A61B 5/0492* (2006.01)

(52) U.S. Cl.
CPC ...... *A61B 5/02416* (2013.01); *A61B 5/02438* (2013.01); *A61B 5/0404* (2013.01); *A61B 5/04012* (2013.01); *A61B 5/04085* (2013.01); *A61B 5/0488* (2013.01); *A61B 5/0492* (2013.01); *A61B 5/04288* (2013.01); *A61B 5/0531* (2013.01); *A61B 5/681* (2013.01); *A61B 5/6824* (2013.01); *A61B 5/7475* (2013.01); *G06F 3/01* (2013.01); *G06F 3/011* (2013.01); *G06F 3/015* (2013.01); *G06F 3/017* (2013.01); *A61B 5/02427* (2013.01); *A61B 2560/0468* (2013.01); *A61B 2562/0209* (2013.01); *A61B 2562/0238* (2013.01); *A61B 2562/046* (2013.01); *A61B 2562/066* (2013.01)

(56) References Cited

U.S. PATENT DOCUMENTS

| | | | | |
|---|---|---|---|---|
| 7,894,888 B2* | 2/2011 | Chan | ................... | A61B 5/0006 600/509 |
| 9,189,901 B2* | 11/2015 | Agrafioti | ................ | G06F 21/40 |
| 2007/0276270 A1 | 11/2007 | Tran | | |
| 2008/0004904 A1* | 1/2008 | Tran | ................... | A61B 5/0006 705/2 |
| 2009/0059730 A1* | 3/2009 | Lyons | ................... | G04G 21/08 368/69 |
| 2012/0245439 A1* | 9/2012 | Andre | ................. | A61B 5/0205 600/310 |
| 2014/0135631 A1* | 5/2014 | Brumback | ......... | A61B 5/02438 600/479 |
| 2014/0257129 A1 | 9/2014 | Choi et al. | | |
| 2015/0124566 A1* | 5/2015 | Lake | ...................... | G04G 21/08 368/10 |
| 2015/0215443 A1* | 7/2015 | Heo | .................... | H04M 1/0202 455/556.1 |
| 2015/0265214 A1 | 9/2015 | Kok et al. | | |
| 2015/0370224 A1* | 12/2015 | Emmert | ................... | A44C 5/14 224/164 |
| 2016/0228064 A1* | 8/2016 | Jung | .................... | G06F 1/1656 |
| 2016/0378965 A1* | 12/2016 | Choe | ...................... | G06F 21/32 726/19 |
| 2017/0215743 A1 | 8/2017 | Meer et al. | | |
| 2017/0238812 A1* | 8/2017 | Atlas | ...................... | G16H 40/67 |

OTHER PUBLICATIONS

"Combined Search and Examination Report", GB Application No. 1621075.9, dated May 25, 2017, 10 pages.

"Non-Final Office Action", U.S. Appl. No. 15/485,108, dated Oct. 9, 2019, 13 pages.

"Foreign Office Action", GB Application No. 1621075.9, dated Nov. 1, 2019, 3 pages.

"Foreign Office Action", GB Application No. 1621075.9, dated Mar. 10, 2020, 4 pages.

* cited by examiner

WEARABLE DEVICE HEART MONITOR SYSTEMS

BACKGROUND

Wearable devices, such as watches and fitness tracking devices, are essentially a small computing device and becoming more popular with users. Generally, a wearable watch device can be used in the traditional sense to track time, and may be used for communication with a user's mobile phone, such as to display received messages, incoming phone calls, calendar appointments, and generally as an extended interface of the mobile phone. Other types of wearable devices that are increasingly popular are fitness tracking and feedback devices that can be implemented with sensors to monitor the heartrate of a user, distance traveled, exercise levels, sleep patterns, and other activities, movement, and personal metrics of a user wearing the device.

Some wearable devices are designed to obtain electrocardiogram (ECG) readings, which provide the user with a reading of heart rate over time and can be used to diagnose potential heart issues. An ECG measures the electrical signal between two extremities, such as from one hand to the other hand, with the electrical signal passing through the heart between the two extremities. Generally, the accuracy and quality of the ECG signal is related to the surface area of the two contacts between which the electrical signal passes, and implementation in a small form-factor wearable device does not provide a reliable ECG reading.

BRIEF DESCRIPTION OF THE DRAWINGS

Embodiments of wearable device heart monitor systems are described with reference to the following Figures. The same numbers may be used throughout to reference like features and components that are shown in the Figures.

DETAILED DESCRIPTION

Figure 1:
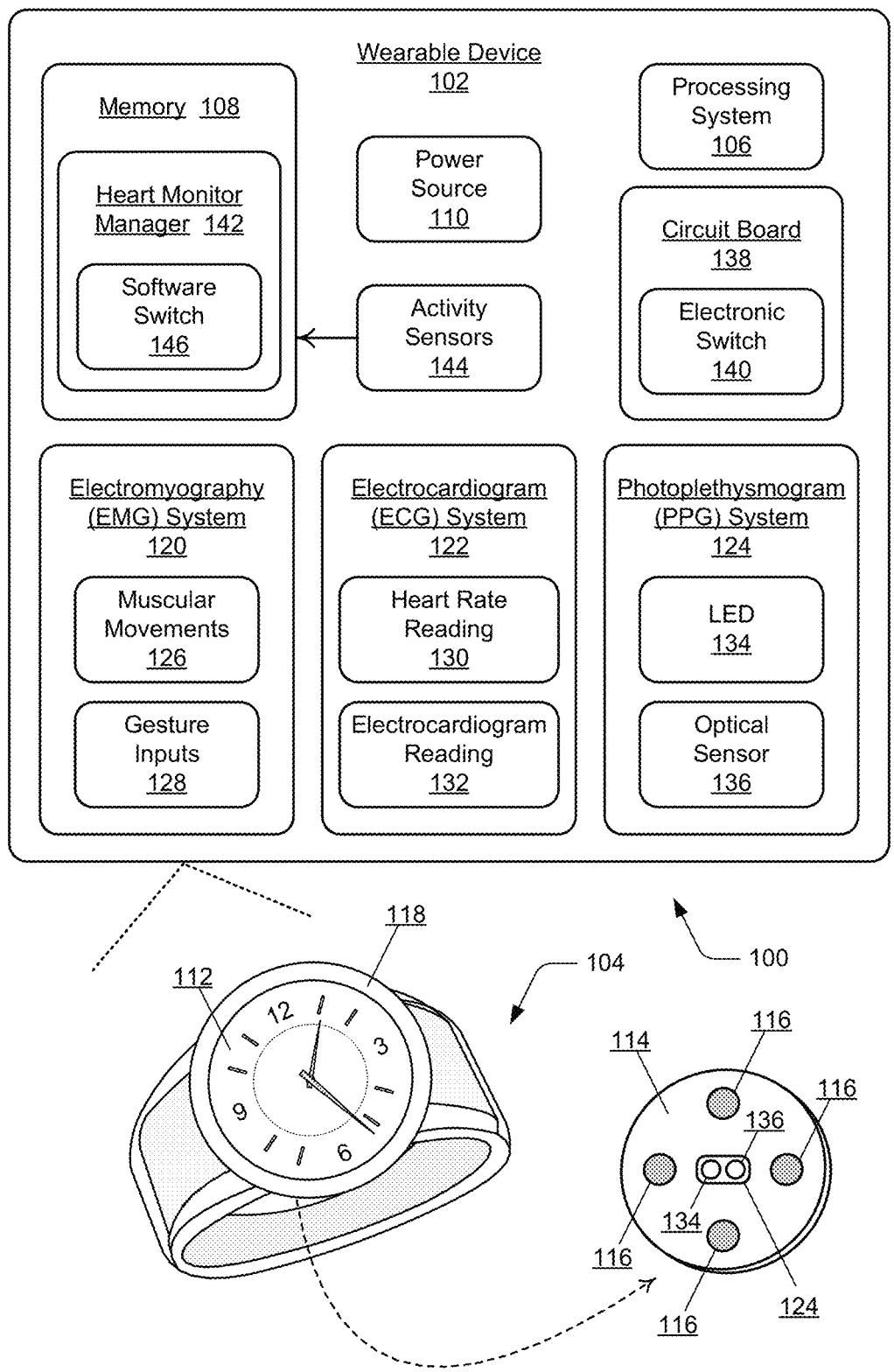
FIG. 1 illustrates an example wearable device in which techniques of wearable device heart monitor systems can be implemented.

Embodiments of wearable device heart monitor systems are described, and provide techniques to implement multiple, different heart monitor systems in a single wearable device, such as a smartwatch device, fitness tracker device, and/or other similar devices. In implementations, a wearable device can include an electromyography (EMG) system, an electrocardiogram (ECG) system, and a photoplethysmogram (PPG) system. The wearable device includes electrical contacts that are integrated in a housing base of the wearable device as electrodes designed to contact the skin of a user while wearing the wearable device. A housing bezel of the wearable device is also designed as an additional point of contact on the wearable device implemented for a heart monitor system of the wearable device.

Electromyography (EMG) is an electro-diagnostic technique for evaluating and recording the electrical activity produced by the skeletal muscles of a user wearing the wearable device. The EMG system uses electrodes to measure the electrical activity of the skeletal muscles, and can be implemented to detect gestures and muscular loading (movements). The photoplethysmogram (PPG) system uses a light emitting diode (LED) to illuminate the skin of the user, and includes an optical sensor to detect reflected light from which heart rate measurements of the user are determined. The PPG system measures the change in light absorption during a cardiac cycle of the heart of the user wearing the wearable device, and a photoplethysmogram indicates blood flow modulated in the skin by the cardiac cycles.

Electrocardiography (ECG), also commonly referred to as EKG, records the electrical activity of the heart over a period of time using the electrodes, which detect the small electrical changes on the skin that occur when the heart muscle depolarizes during each heartbeat. The readings from the ECG system allow for an accurate heart rate reading and can be used to measure the rate and rhythm of heartbeats, as well as diagnose potential heart issues. The ECG system can measure or determine the heart rate reading over time by measuring the combined electrical signals between a first extremity of the user in contact with the electrodes, through the heart of the user, and a second extremity of the user in contact with a housing bezel of the wearable device. In implementations, the ECG system can receive and combine the electrical signals from the electrodes when the user touch contacts the housing bezel with one hand while wearing the wearable device on the wrist of the opposite hand to complete an ECG loop between the electrodes and the housing bezel for a heart rate reading of the user.

In implementations, a wearable device that includes the multiple, different heart monitor systems balances the design needs for the systems by utilizing four electrical contacts as the electrodes to measure the EMG system electrical signals, and utilizes an electrical and/or software switch to combine the electrical signals from the electrodes acting as a single sensor with a larger surface area for the ECG system measurements. As noted above, the housing bezel of the wearable device is a grounded connection designed as the other point of contact implemented for the ECG system to obtain the heart readings when the user touch contacts the housing bezel with one hand while wearing the wearable device on the wrist of the opposite hand to complete an ECG loop between the electrodes and the housing bezel.

While features and concepts of wearable device heart monitor systems can be implemented in any number of different devices, systems, environments, and/or configurations, embodiments of wearable device heart monitor systems are described in the context of the following example devices, systems, and methods.

FIG. 1 illustrates an example 100 of a wearable device 102 in which techniques of wearable device heart monitor systems can be implemented. In this example, the wearable device 102 may be any type of portable electronic and/or computing device, such as a fitness tracker and/or watch device shown at 104 that is itself implemented as a small computing device, smart device, or smartwatch. The wearable device 102 can be implemented with various components, such as a processing system 106 and memory 108, as well as any number and combination of differing components as further described with reference to the example device shown in FIG. 8. For example, the wearable device 102 can include a power source 110 to power the device, such as a flexible strip battery, a rechargeable battery, and/or any other type of active or passive power source that may be implemented in a wearable device.

The example wearable device 102 has an integrated display 112 to display a user interface of the wearable device, such as to display the current time and date when the wearable device is used in the traditional sense as a watch (e.g., shown at 104). The integrated display 112 can also be implemented to display received messages, incoming phone calls, calendar appointments, heart rate readings, heart measurements, electrocardiogram readings (commonly referred to as an EKG), and any other displayable charts and information.

The wearable device 102 includes electrical contacts that are integrated in a housing base 114 of the wearable device as electrodes 116 designed to contact the skin of a user while wearing the wearable device. In implementations, the electrical contacts (e.g., the electrodes 116) are equally spaced and arranged in a pattern in the housing base 114 that allows any combination of the electrical contacts being utilized by a heart monitor system of the wearable device. Additionally, the surface area of the electrical contacts is minimized so as not to interfere with the wireless communication system antennas of the wearable device. Although not shown, the wearable device 102 may be implemented with one or more communication systems, such as Bluetooth™, GPS, Wi-Fi, and similar systems that each include a radio device, antenna, and chipset implemented for wireless and data network communication with the other devices.

A housing bezel 118 of the wearable device 102 is designed as an additional point of contact on the wearable device implemented for a heart monitor system of the wearable device. In this example, the wearable device 102 is implemented with multiple heart monitor systems, such as an electromyography (EMG) system 120, an electrocardiogram (ECG) system 122, and a photoplethysmogram (PPG) system 124. As noted above, the surface area of the electrical contacts is minimized in the housing base 114, providing space for the components of the PPG system 124 as shown at 104.

Electromyography (EMG) is an electro-diagnostic technique for evaluating and recording the electrical activity produced by the skeletal muscles of the user of the wearable device. The EMG system 120 uses the electrodes 116 to measure the electrical activity of the skeletal muscles and can be used to detect gestures and muscular loading (movements). The EMG system 120 can receive electrical signals from at least two of the electrodes 116 and detect muscular movements 126 of the user. As noted above, the electrodes 116 are equally spaced and arranged in a pattern in the housing base 114 that allows any combination of the electrodes being utilized by the EMG system. However, using more of the electrodes 116 will increase the reliability of the readings, as well as reduce false readings due to user movement.

The EMG system 120 is also implemented to determine gesture inputs 128 to the wearable device 102 based on the detected muscular movements 126 of the user. Generally, the determined gesture inputs may be as simple as a device wakeup input, or may be more complicated muscular movement detections, such as the user doing pushups and the EMG system 120 sensing muscular loading of the user's wrists, or the user lifting something and the EMG system detecting that the user's hand is clenched or open. Other determinable gestures based on detected muscular loading can include finger snapping, multiple finger movements, and many other types of movements initiated by the user to interact with the wearable device.

Electrocardiography (ECG), also commonly referred to as EKG, records the electrical activity of the heart over a period of time using the electrodes 116, which detect the small electrical changes on the skin that occur when the heart muscle depolarizes during each heartbeat. The readings from the ECG system 122 allow for an accurate heart rate reading 130 and can be used to measure the rate and rhythm of heartbeats, as well as diagnose potential heart issues. The ECG system 122 can measure or determine the heart rate reading over time by measuring the combined electrical signals between a first extremity of the user in contact with the electrodes 116, through the heart of the user, and a second extremity of the user in contact with the housing bezel 118 of the wearable device.

In implementations, the ECG system 122 can receive and combine the electrical signals from the electrodes 116 when the user touch contacts the housing bezel 118 with one hand while wearing the wearable device on the wrist of the opposite hand to complete an ECG loop between the electrodes 116 and the housing bezel 118 for a heart rate reading 130 of the user. The ECG system 122 can also determine an electrocardiogram reading 132 of the user, and the ECG readings can be displayed as a graph or other representation on the integrated display 112 of the wearable device, or communicated for display on another device of the user, such as on a mobile phone.

The photoplethysmogram (PPG) system 124 includes a light emitting diode (LED) 134 to illuminate the skin of the user, and includes an optical sensor 136 to detect reflected light from which heart rate measurements of the user are determined. The PPG system 124 measures the change in light absorption during a cardiac cycle of the heart of the user wearing the wearable device 102, and a photoplethysmogram indicates blood flow modulated in the skin by the cardiac cycles. A heart rate measurement of the user wearing the wearable device 102 can be determined without the user having to touch or contact the wearable device with both hands. Further, the PPG system 124 may be initiated or activated based on an accelerometer input that indicates user activity, such as if the user begins walking or jogging.

In embodiments, the wearable device 102 includes a circuit board 138 that is implemented to couple the electrodes 116 to the EMG system 120 and to the ECG system 122. The housing bezel 118 is also grounded to the circuit board 138 to complete the ECG loop between the electrodes 116 and the housing bezel when the user touch contacts the housing bezel while wearing the wearable device. The technique implemented to ground the housing bezel 118 as the additional point of contact for the ECG system eliminates the need for an additional, independent component of the wearable device. In implementations, the circuit board 138 includes an electronic switch 140 integrated in the circuit board to dynamically switch between the EMG system 120 and the ECG system 122 based on detected user activity. Further, the circuit board 138 can combine the electrical signals from the electrodes 116 to complete the ECG loop for the heart rate reading of the user. Alternatively, a software application may be implemented in the wearable device 102 to combine the electrical signals from the electrodes 116 to complete the ECG loop for the ECG system.

In embodiments, the wearable device 102 can include a heart monitor manager 142 implemented as a software application or module, such as executable software instructions (e.g., computer-executable instructions) that are executable with the processing system 106 of the wearable device. The heart monitor manager 142 can be stored on computer-readable storage memory, such as any suitable memory 108 or electronic data storage implemented by the wearable device. As noted above, the heart monitor manager 142 can be implemented to combine the electrical signals from the electrodes 116 to complete the ECG loop for the ECG system, and determine the heart rate reading 130 of the user. In this example, the heart monitor manager 142 can detect user activity based on sensor inputs from activity sensors 144, such as an accelerometer, GPS system, light sensor, and any other types of sensors or systems that are indicative of user activity while the user is wearing the wearable device. The heart monitor manager 142 also includes a software switch 146 implemented to dynamically switch between the EMG system and the ECG system, and optionally activate the PPG system based on the detected user activity. In implementations, the PPG system can perform independently from the EMG system and/or the ECG system. Further, the user does not have to manually initiate the different modes, although the design can also provide for user-initiated heart sensor modes.

In embodiments, the heart monitor manager 142 is a component of one or more of the heart monitor systems in the wearable device 102, such as a component of the EMG system 120, the ECG system 122, and/or the PPG system 124. As a component of the EMG system 120, the heart monitor manager 142 can be implemented to detect the muscular movements 126 of the user based on the received electrical signals from the electrodes 116, and determine the gesture inputs 128 to the wearable device 102 based on the detected muscular movements 126 of the user. As a component of the ECG system 122, the heart monitor manager 142 can also be implemented to determine the heart rate reading 130, as well as the electrocardiogram reading 132. As a component of the PPG system 124, the heart monitor manager 142 can also be implemented to determine the heart rate measurements of the user based on the emitted and reflected light that is detected by the optical sensor 136 of the PPG system.

Example methods 200 and 300 are described with reference to respective FIGS. 2 and 3 in accordance with implementations of wearable device heart monitor systems. Generally, any services, components, modules, methods, and/or operations described herein can be implemented using software, firmware, hardware (e.g., fixed logic circuitry), manual processing, or any combination thereof. Some operations of the example methods may be described in the general context of executable instructions stored on computer-readable storage memory that is local and/or remote to a computer processing system, and implementations can include software applications, programs, functions, and the like. Alternatively or in addition, any of the functionality described herein can be performed, at least in part, by one or more hardware logic components, such as, and without limitation, Field-programmable Gate Arrays (FPGAs), Application-specific Integrated Circuits (ASICs), Application-specific Standard Products (ASSPs), System-on-a-chip systems (SoCs), Complex Programmable Logic Devices (CPLDs), and the like.

Figure 2:
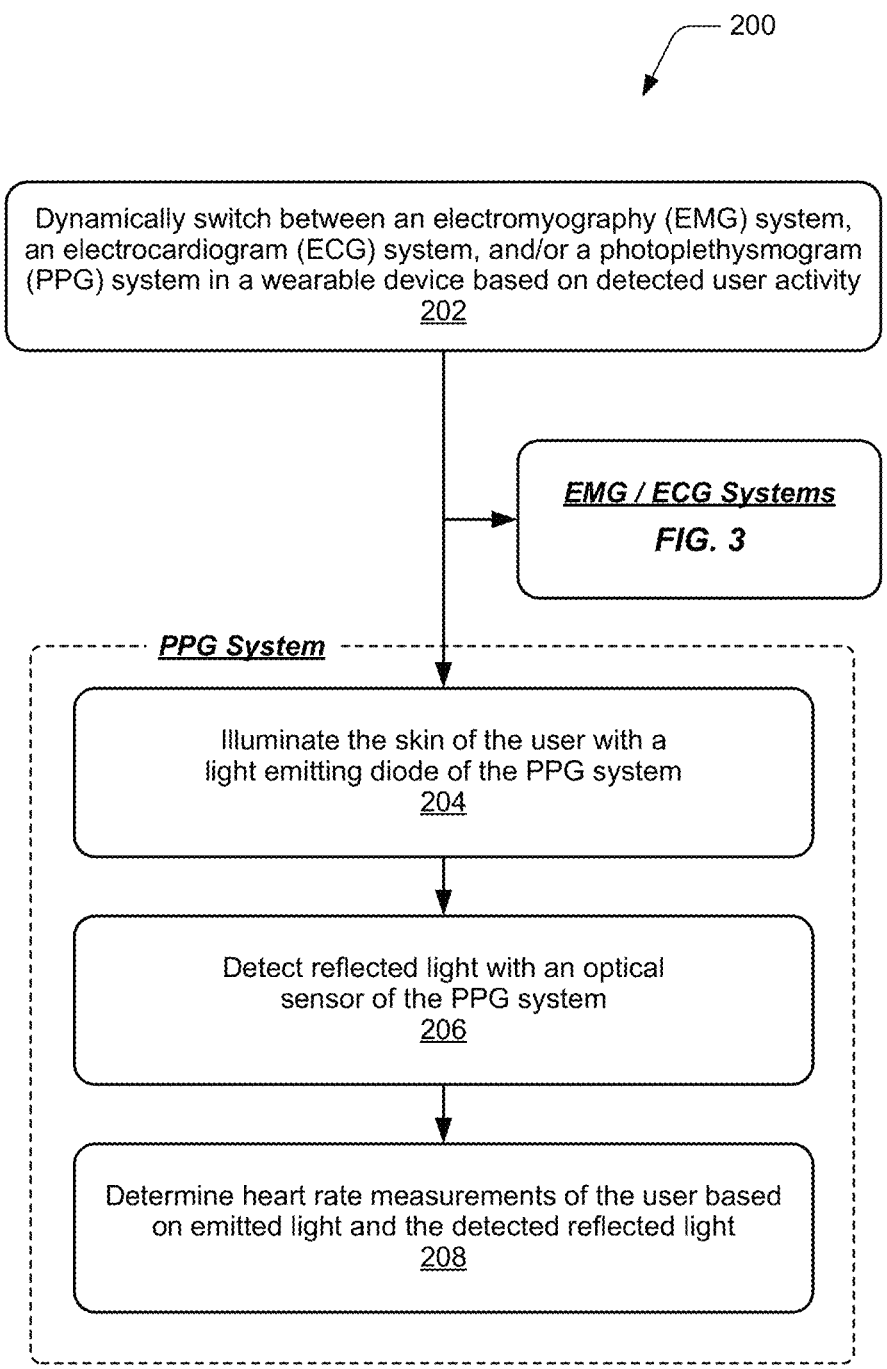
FIG. 2 illustrates example method(s) of wearable device heart monitor systems in accordance with one or more embodiments.

FIG. 2 illustrates example method(s) 200 of the heart monitor systems in embodiments of wearable device heart monitor systems. The order in which the method is described is not intended to be construed as a limitation, and any number or combination of the described method operations can be performed in any order to perform a method, or an alternate method.

At 202, heart monitor systems are dynamically switched between an electromyography (EMG) system, an electrocardiogram (ECG) system, and/or a photoplethysmogram (PPG) system in a wearable device based on detected user activity. For example, the wearable device 102 includes multiple heart monitor systems, such as the EMG system 120, the ECG system 122, and the PPG system 124. The heart monitor manager 142 that is implemented in the wearable device 102 includes the software switch 146 to dynamically switch between the EMG system 120 and the ECG system 122, and optionally activates the PPG system 124 based on detected user activity, such as activity of the user detected by the activity sensors 144 while the user is wearing the wearable device. In implementations, the PPG system can perform in conjunction with, or independently from, the EMG system and/or the ECG system.

The method 200 continues if the PPG system is switch-selected or activated. Alternatively, if the EMG system or the ECG system is switch-selected or activated, then a method 300 described with reference to FIG. 3 is initiated. At 204, the skin of the user is illuminated with a light emitting diode of the PPG system; at 206, reflected light is detected with an optical sensor of the PPG system; and at 208, heart rate measurements of the user are determined based on the emitted light and the detected reflected light. For example, the light emitting diode (LED) 134 of the PPG system 124 illuminates the skin of the user wearing the wearable device, and the optical sensor 136 detects reflected light from which heart rate measurements of the user are determined. In embodiments, the heart monitor manager 142 is implemented as a component of the PPG system 124 and determines the heart rate measurements of the user based on the reflected light readings.

Figure 3:
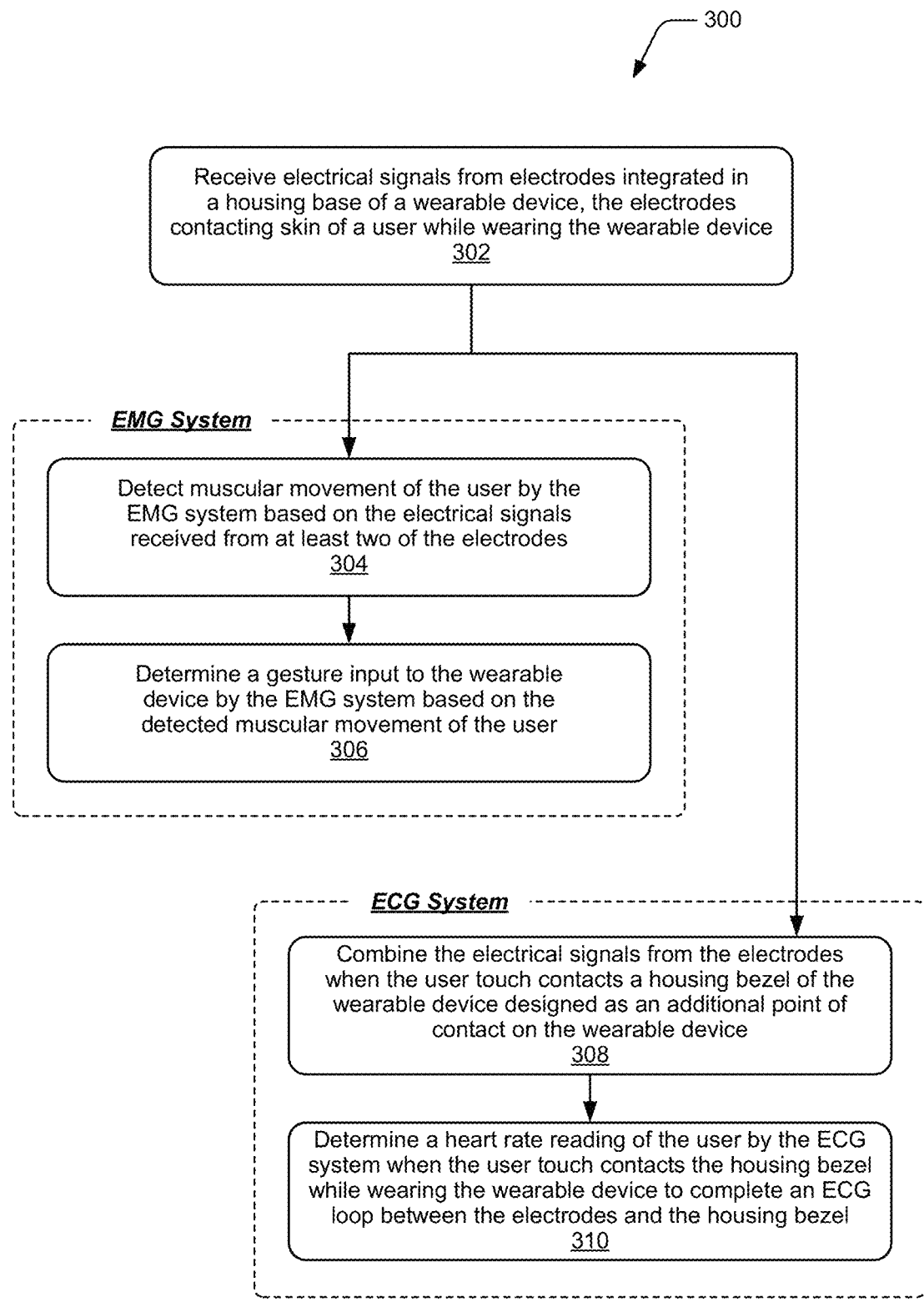
FIG. 3 illustrates example method(s) of wearable device heart monitor systems in accordance with one or more embodiments.

FIG. 3 illustrates example method(s) 300 of the heart monitor systems in embodiments of wearable device heart monitor systems. The order in which the method is described is not intended to be construed as a limitation, and any number or combination of the described method operations can be performed in any order to perform a method, or an alternate method.

At 302, electrical signals are received from electrodes integrated in a housing base of a wearable device, the electrodes contacting skin of a user while wearing the wearable device. For example, the wearable device 102 includes the electrical contacts that are integrated in a housing base 114 of the wearable device as the electrodes 116 designed to contact the skin of a user while wearing the wearable device. The circuit board 138 and/or the heart monitor manager 142 receives the electrical signals from the electrodes 116, which are equally spaced and arranged in a pattern that allows any combination of at least two of the electrodes being utilized by the EMG system 120. The circuit board 138 couples the electrodes to the EMG system 120 and to the ECG system 122, and combines the electrical signals from the electrodes with the electronic switch 140 to complete the ECG loop for the heart rate reading of the user. Further, the housing bezel 118 of the wearable device 102 is grounded to the circuit board 138 to complete the ECG loop between the electrodes 116 and the housing bezel 118 when the user touch contacts the housing bezel while wearing the wearable device.

With reference to the EMG system 120, at 304, muscular movement of the user is detected by the EMG system based on the electrical signals received from at least two of the electrodes. For example, the EMG system 120 receives the electrical signals from at least two of the electrodes 116 and detects the muscular movements 126 of the user. At 306, a gesture input to the wearable device is determined by the EMG system based on the detected muscular movement of the user. For example, the EMG system 120 determines the gesture inputs 128 to the wearable device 102 based on the detected muscular movements 126 of the user. In embodiments, the heart monitor manager 142 is implemented as a component of the EMG system 120 and determines the muscular movements 126 of the user based on the received electrical signals, and determines the gesture inputs 128 to the wearable device 102 based on the detected muscular movements 126 of the user.

With reference to the ECG system 122, at 308, the electrical signals from the electrodes are combined when the user touch contacts a housing bezel of the wearable device designed as an additional point of contact on the wearable device. At 310, a heart rate reading of the user is determined by the ECG system when the user touch contacts the housing bezel while wearing the wearable device to complete an ECG loop between the electrodes and the housing bezel. For example, the ECG system 122 receives and combines the electrical signals from the electrodes 116 when the user touch contacts the housing bezel 118 with one hand while wearing the wearable device on the wrist of the opposite hand to complete the ECG loop between the electrodes 116 and the housing bezel 118 for a heart rate reading 130 of the user. The ECG system 122 determines the heart rate reading over time by measuring the combined electrical signals between a first extremity of the user in contact with the electrodes, through the heart of the user, and a second extremity of the user in contact with the housing bezel. The ECG system 122 also determines the electrocardiogram reading 132 of the user. In embodiments, the heart monitor manager 142 is implemented as a component of the ECG system 122 and determines the heart rate reading 130 of the user, as well as the electrocardiogram reading 132 of the user.

Figure 4:
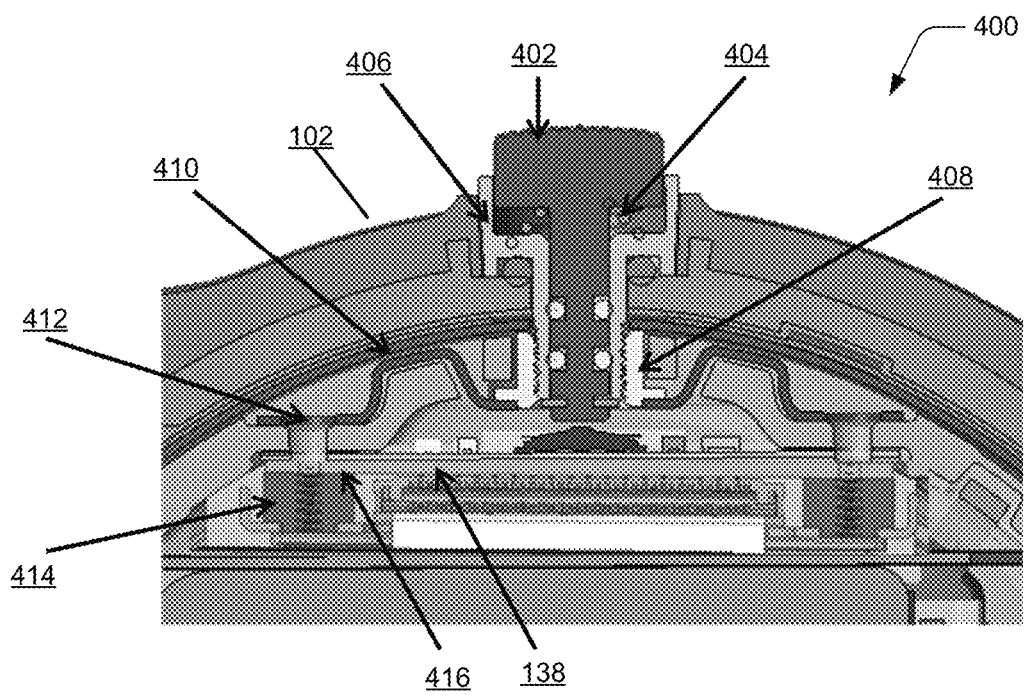
FIGS. 4-7 illustrate component detail views of an example wearable device in embodiments of wearable device heart monitor systems.

FIGS. 4-7 illustrate component detail views of the example wearable device 102. In particular, FIG. 4 illustrates a component detail view 400 of a section of the wearable device 102, and illustrates a ground path for the device power key 402 to the circuit board 138. The component detail view 400 includes the power key 402, a spring 404, a bushing 406, a first insert 408, a bracket 410, a screw 412, a second insert 414, and a gold pad 416 on the circuit board 138. In implementations, this sequence of wearable device components is the ground path for the device power key 402 to the circuit board 138.

Figure 5:
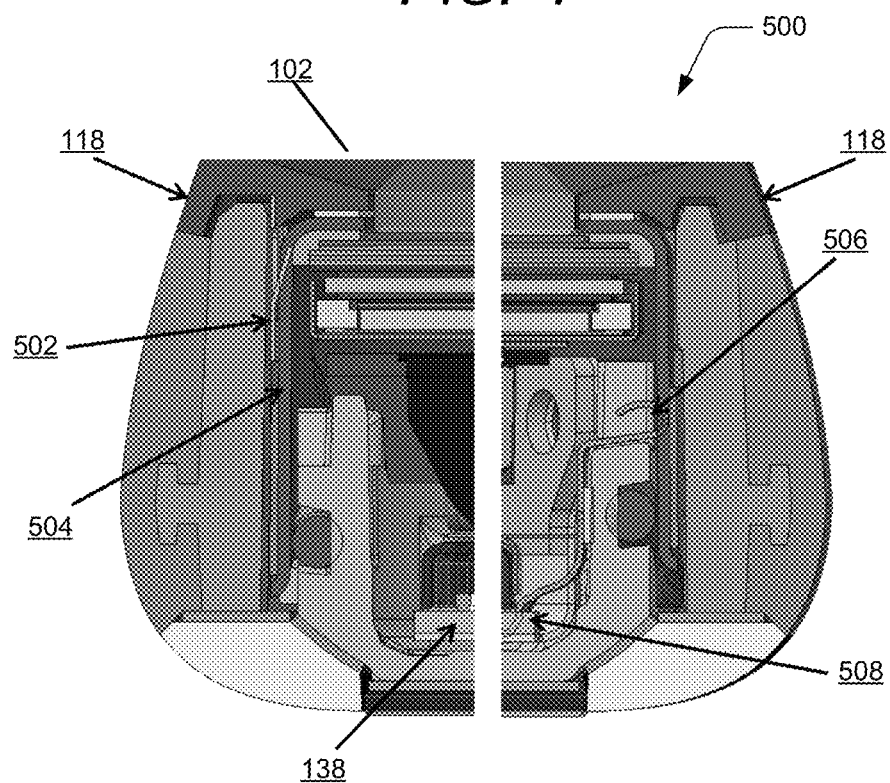

FIG. 5 illustrates a component detail view 500 of a section of the wearable device 102, and illustrates a ground path for the housing bezel 118 to the circuit board 138. The component detail view 500 includes the housing bezel 118, a ground clip 502, a puck housing 504, a printed circuit board (PCB) ground 506, and a gold pad 508 on the circuit board 138. In implementations, this sequence of wearable device components is the ground path for the housing bezel 118 to the circuit board 138.

Figure 6:
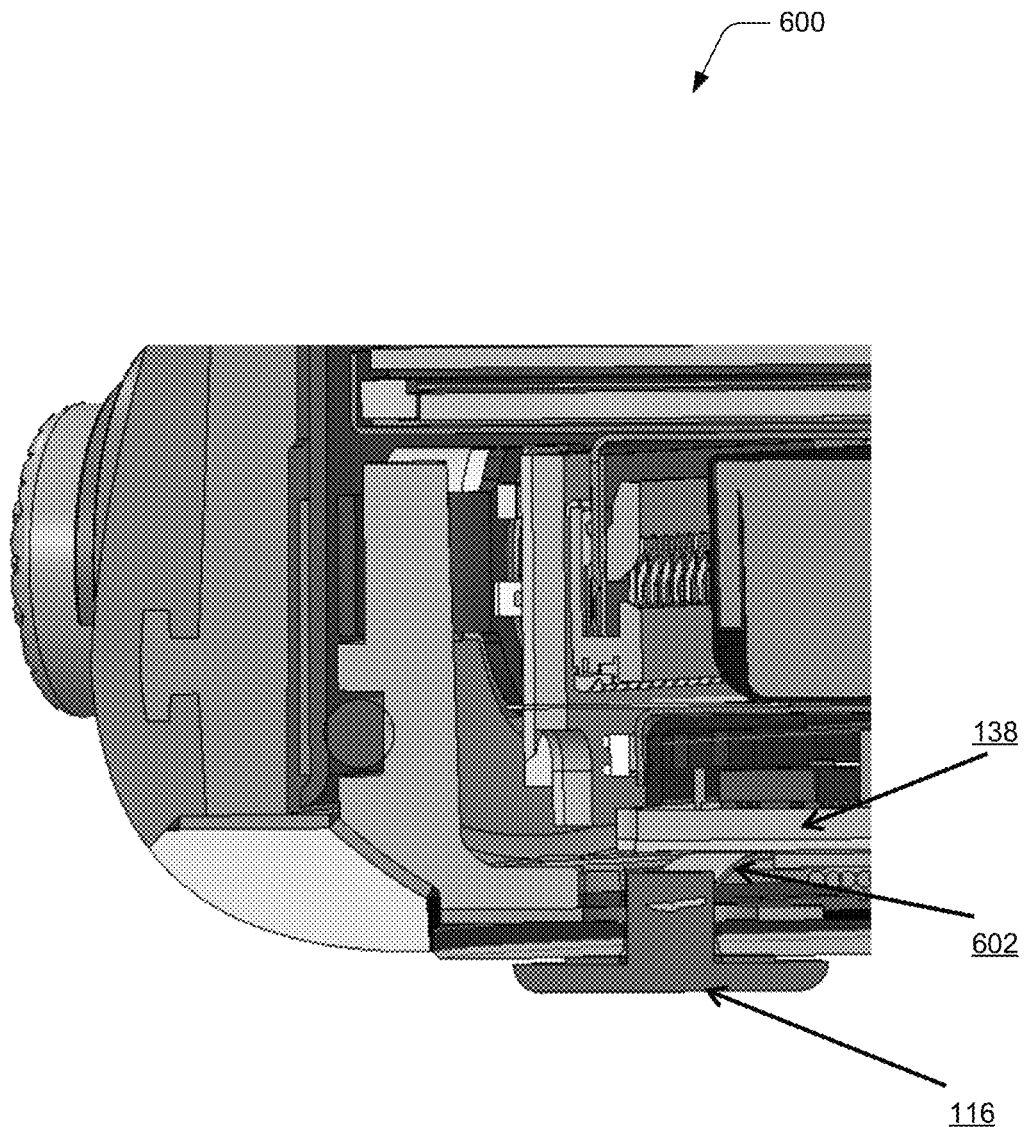

FIG. 6 illustrates a component detail view 600 of a section of the wearable device 102, and illustrates a ground path from the circuit board 138 (e.g., a printed circuit board (PCB)) to an electrode 116 (e.g., an electrical contact integrated in the housing base 114 of the wearable device 102). The component detail view 600 includes the circuit board 138, a contact clip 602, and an electrode 116. In implementations, this sequence of wearable device components is the ground path from the circuit board 138 to an electrode 116 that is integrated in the housing base 114 of the wearable device 102.

Figure 7:
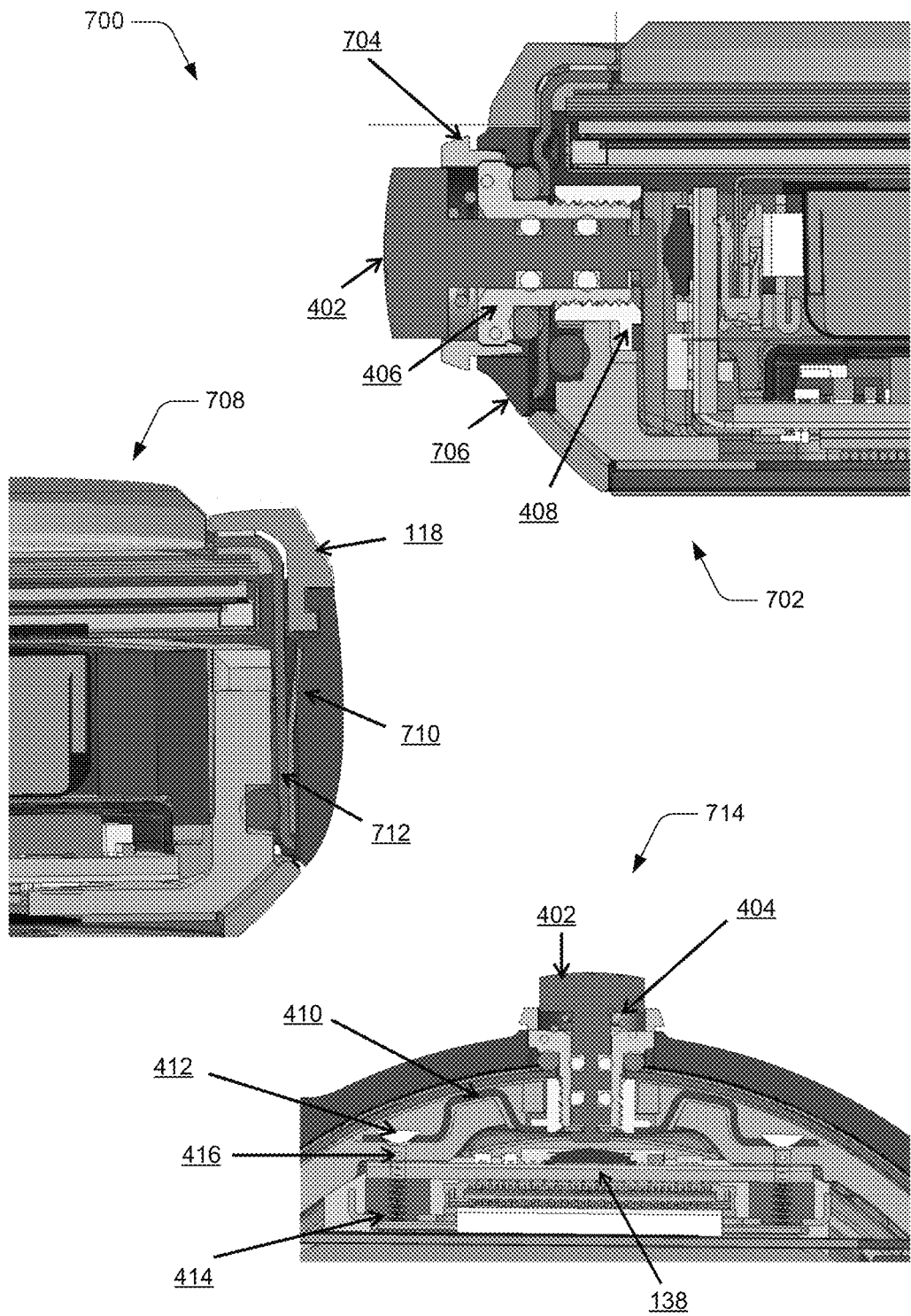

FIG. 7 illustrates component detail views 700 of sections of the wearable device 102, and illustrates a similar ground path for the power key 402, a collar, and the housing bezel 118 to ground (e.g., the circuit board 138). A first component detail view 702 includes the collar 704, the bushing 406, a cosmetic front 706, and the first insert 408. A second component detail view 708 includes the housing bezel 118, a brace 710, and a shell 712. A third component detail view 714 includes the power key 402, the spring 404, the bracket 410, the screw 412, the second insert 414, and the gold pad 416 on the circuit board 138. In implementations, the sequence of the ground path for the power key 402 to ground is the power key 402, the spring 404, the bushing 406, the first insert 408, the bracket 410, the second insert 414, and the gold pad 416 on the circuit board 138. The sequence of the ground path for the collar 704 to ground is the bushing 406, the first insert 408, the bracket 410, the second insert 414, and the gold pad 416 on the circuit board 138. The sequence of the ground path for the housing bezel 118 to ground is the cosmetic front 706, the bushing 406, the first insert 408, the bracket 410, the second insert 414, and the gold pad 416 on the circuit board 138.

Figure 8:
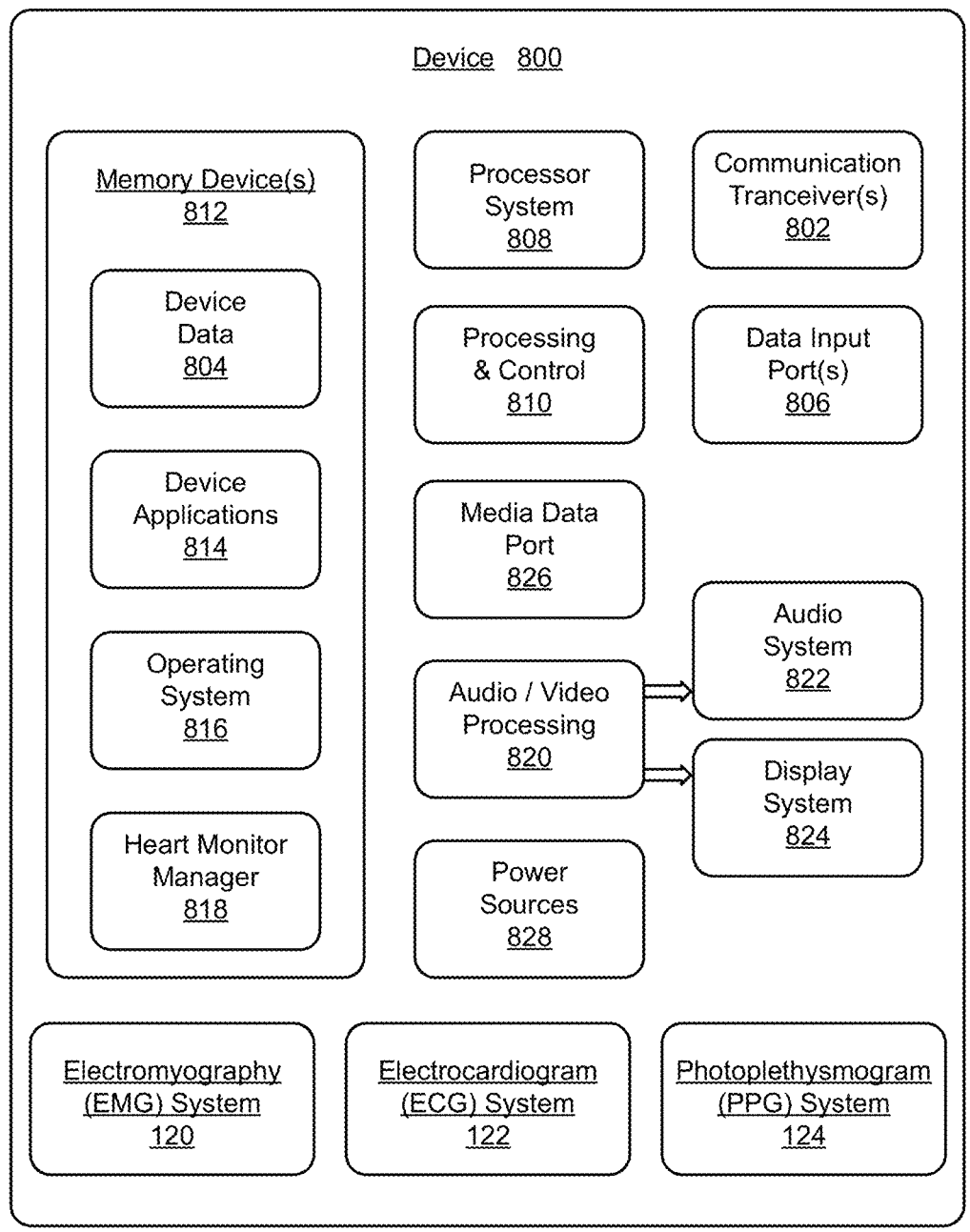
FIG. 8 illustrates various components of an example device that can implement embodiments of wearable device heart monitor systems.

FIG. 8 illustrates various components of an example device 800 in which embodiments of wearable device heart monitor systems can be implemented. The example device 800 can be implemented as any type of wearable device, client device, mobile device, computing, communication, fitness, entertainment, gaming, media playback, and/or other type of device. For example, the wearable device 102 shown and described with reference to FIGS. 1-7 may be implemented as the example device 800.

The device 800 includes communication transceivers 802 that enable wired and/or wireless communication of device data 804 with other devices. The device data 804 can include any of the heart data that is detected and/or determined by any one or more of the electromyography (EMG) system 120, the electrocardiogram (ECG) system 122, and the photoplethysmogram (PPG) system 124. Additionally, the device data can include any type of audio, video, and/or image data. Example transceivers include wireless personal area network (WPAN) radios compliant with various IEEE 802.15 (Bluetooth™) standards, wireless local area network (WLAN) radios compliant with any of the various IEEE 802.11 (WiFi™) standards, wireless wide area network (WWAN) radios for cellular phone communication, wireless metropolitan area network (WMAN) radios compliant with various IEEE 802.15 (WiMAX™) standards, and wired local area network (LAN) Ethernet transceivers for network data communication.

The device 800 may also include one or more data input ports 806 via which any type of data, media content, and/or inputs can be received, such as user-selectable inputs to the device, messages, music, television content, and any other type of audio, video, and/or image data received from any content and/or data source. The data input ports may include USB ports, coaxial cable ports, and other serial or parallel connectors (including internal connectors) for flash memory, DVDs, CDs, and the like. These data input ports may be used to couple the device to any type of components, peripherals, or accessories such as microphones and/or cameras.

The device 800 includes a processing system 808 of one or more processors (e.g., any of microprocessors, controllers, and the like) and/or a processor and memory system implemented as a system-on-chip (SoC) that processes computer-executable instructions. The processor system may be implemented at least partially in hardware, which can include components of an integrated circuit or on-chip system, an application-specific integrated circuit (ASIC), a field-programmable gate array (FPGA), a complex programmable logic device (CPLD), and other implementations in silicon and/or other hardware. Alternatively or in addition, the device can be implemented with any one or combination of software, hardware, firmware, or fixed logic circuitry that is implemented in connection with processing and control circuits, which are generally identified at 810. The device 800 may further include any type of a system bus or other data and command transfer system that couples the various components within the device. A system bus can include any one or combination of different bus structures and architectures, as well as control and data lines.

The device 800 also includes computer-readable storage memory 812 that enable data storage, such as data storage devices that can be accessed by a computing device, and that provide persistent storage of data and executable instructions (e.g., software applications, programs, functions, and the like). Examples of the computer-readable storage memory 812 include volatile memory and non-volatile memory, fixed and removable media devices, and any suitable memory device or electronic data storage that maintains data for computing device access. The computer-readable storage memory can include various implementations of random access memory (RAM), read-only memory (ROM), flash memory, and other types of storage media in various memory device configurations. The device 800 may also include a mass storage media device.

The computer-readable storage memory 812 provides data storage mechanisms to store the device data 804, other types of information and/or data, and various device applications 814 (e.g., software applications). For example, an operating system 816 can be maintained as software instructions with a memory device and executed by the processing system 808. The device applications may also include a device manager, such as any form of a control application, software application, signal-processing and control module, code that is native to a particular device, a hardware abstraction layer for a particular device, and so on. In this example, the device 800 includes a heart monitor manager 818 that implements embodiments of wearable device heart monitor systems, and may be implemented with hardware components and/or in software, such as when the device 800 is implemented as the wearable device 102 described with reference to FIGS. 1-7.

The device 800 also includes an audio and/or video processing system 820 that generates audio data for an audio system 822 and/or generates display data for a display system 824. The audio system and/or the display system may include any devices that process, display, and/or otherwise render audio, video, display, and/or image data. Display data and audio signals can be communicated to an audio component and/or to a display component via an RF (radio frequency) link, S-video link, HDMI (high-definition multimedia interface), composite video link, component video link, DVI (digital video interface), analog audio connection, or other similar communication link, such as media data port 826. In implementations, the audio system and/or the display system are integrated components of the example device. Alternatively, the audio system and/or the display system are external, peripheral components to the example device.

The device 800 can also include one or more power sources 828, such as when the device is implemented as a mobile device. The power sources may include a charging and/or power system, and can be implemented as a flexible strip battery, a rechargeable battery, a charged super-capacitor, and/or any other type of active or passive power source.

Although embodiments of wearable device heart monitor systems have been described in language specific to features and/or methods, the subject of the appended claims is not necessarily limited to the specific features or methods described. Rather, the specific features and methods are disclosed as example implementations of wearable device heart monitor systems, and other equivalent features and methods are intended to be within the scope of the appended claims. Further, various different embodiments are described and it is to be appreciated that each described embodiment can be implemented independently or in connection with one or more other described embodiments.

The invention claimed is:

1. A wearable device, comprising:
   electrical contacts integrated in a housing base of the wearable device as electrodes configured to contact skin of a user while the user is wearing the wearable device, each of the electrodes being a point of contact on the wearable device;
   a housing bezel of the wearable device configured as an additional point of contact on the wearable device, the housing bezel grounded to a circuit board via a sequential ground path from the housing bezel to a ground clip and an internal puck housing, and via a ground connecting the internal puck housing to a gold pad on the circuit board;
   an electromyography (EMG) system configured to receive electrical signals from at least two of the electrodes and detect muscular movement of the user;
   an electrocardiogram (ECG) system configured to receive the electrical signals from the electrodes in response to the user contacting the housing bezel while wearing the wearable device to complete an ECG loop between the electrodes and the housing bezel for a heart rate reading of the user; and
   a memory and processing system that implements a heart monitor manager configured to control combining the electrical signals from the electrodes to complete the ECG loop of the ECG system and determine the heart rate reading of the user.

2. The wearable device as recited in claim 1, further comprising a photoplethysmogram (PPG) system that includes a light emitting diode configured to illuminate the skin of the user and an optical sensor configured to detect reflected light from which heart rate measurements of the user are determined.

3. The wearable device as recited in claim 2, wherein the heart monitor manager is configured to:
   dynamically switch between the EMG system and the ECG system based on detected user activity; and
   activate the PPG system in conjunction with, or independently from, the EMG system or the ECG system.

4. The wearable device as recited in claim 1, wherein the heart monitor manager is configured to determine a gesture input to the wearable device based on the muscular movement of the user detected by the EMG system.

5. The wearable device as recited in claim 1, wherein the heart monitor manager is configured to determine the heart rate reading over time based on the combined electrical signals between a first extremity of the user in contact with the electrodes, through a heart of the user, and a second extremity of the user in contact with the housing bezel.

6. The wearable device as recited in claim 5, wherein the heart monitor manager is further configured to determine an electrocardiogram reading of the user.

7. The wearable device as recited in claim 1, wherein the electrodes are equally spaced and arranged in a pattern configured to facilitate any combination of the electrodes being utilized as the at least two electrodes by the EMG system.

8. The wearable device as recited in claim 1, further comprising:
an electronic switch integrated in the circuit board and controlled by the heart monitor manager, the electronic switch configured to combine the electrical signals from the electrodes to complete the ECG loop for the heart rate reading of the user.

9. The wearable device as recited in claim 8, wherein the housing bezel is grounded to the circuit board to complete the ECG loop between the electrodes and the housing bezel in response to the user contacting the housing bezel while wearing the wearable device.

10. A heart sensor assembly, comprising:
electrodes configured to contact skin of a user while the user is wearing a wearable device that includes the heart sensor assembly, each of the electrodes being a point of contact on the wearable device, which includes a housing bezel configured as an additional point of contact of the heart sensor assembly;
an electromyography (EMG) system configured to receive electrical signals from a subset of the electrodes and detect muscular movement of the user in response to the subset of the electrodes contacting the skin of the user;
an electrocardiogram (ECG) system configured to receive the electrical signals from the electrodes in response to the user contacting the housing bezel of the wearable device while wearing the wearable device to complete an ECG loop between the electrodes and the housing bezel for a heart rate reading of the user;
a circuit board configured to couple the subset of the electrodes to the EMG system and couple the electrodes to the ECG system, the housing bezel grounded to the circuit board via a sequential ground path from the housing bezel to a ground clip and an internal puck housing, and via a ground connecting the internal puck housing to a gold pad on the circuit board; and
a heart monitor manager implemented at least partially in hardware and configured to control combining the electrical signals from the electrodes to complete the ECG loop of the ECG system and determine the heart rate reading of the user.

11. The heart sensor assembly as recited in claim 10, further comprising:
a photoplethysmogram (PPG) system that includes a light emitting diode configured to illuminate the skin of the user and an optical sensor configured to detect reflected light from which heart rate measurements of the user are determined.

12. The heart sensor assembly as recited in claim 10, wherein the heart monitor manager is configured to dynamically switch between the EMG system and the ECG system based on detected user activity, and activate the PPG system in conjunction with, or independently from, the EMG system or the ECG system.

13. The heart sensor assembly as recited in claim 10, wherein the heart monitor manager is configured to determine the heart rate reading over time based on the combined electrical signals between a first extremity of the user in contact with the electrodes, through a heart of the user, and a second extremity of the user in contact with the housing bezel of the wearable device.

14. The heart sensor assembly as recited in claim 10, further comprising a switch controlled by the heart monitor manager to switch between the EMG system and the ECG system based on user activity.

15. A wearable device, comprising:
electrodes configured to contact skin of a user while the user is wearing the wearable device, each of the electrodes configured as a point of contact on the wearable device;
a housing bezel of the wearable device configured as an additional point of contact on the wearable device;
an electromyography (EMG) system configured to receive electrical signals from a subset of the electrodes;
an electrocardiogram (ECG) system configured to receive the electrical signals from the electrodes in response to the user contacting the housing bezel while wearing the wearable device;
a circuit board configured to couple the subset of the electrodes to the EMG system and couple the electrodes to the ECG system, the housing bezel grounded to the circuit board via a sequential ground path from the housing bezel to a ground clip and an internal puck housing, and via a ground connecting the internal puck housing to a gold pad on the circuit board;
a memory and processing system that implements a heart monitor manager configured to:
detect muscular movement of the user based on the electrical signals received by the EMG system; and
control combining the electrical signals received from the electrodes by the ECG system in response to the user contacting the housing bezel of the wearable device while wearing the wearable device, the housing bezel being grounded to the circuit board that couples the electrodes to the ECG system to complete an ECG loop between the electrodes and the housing bezel for a heart rate reading of the user.

16. The wearable device as recited in claim 15, wherein the heart monitor manager is configured to determine the heart rate reading over time based on the combined electrical signals between a first extremity of the user in contact with the electrodes, through a heart of the user, and a second extremity of the user in contact with the housing bezel.

17. The wearable device as recited in claim 15, further comprising a housing base configured to integrate the electrodes in the housing base of the wearable device.

18. The wearable device as recited in claim 15, wherein the heart monitor manager is further configured to determine gesture inputs based on the detected muscular movements of the user.

19. The wearable device as recited in claim 15, wherein the heart monitor manager comprises a software switch that is configured to:
dynamically switch between the EMG system and the ECG system; and
activate a photoplethysmogram (PPG) system in conjunction with, or independently from, the EMG system or the ECG system.

20. The wearable device as recited in claim 19, wherein the PPG system includes a light emitting diode configured to illuminate the skin of the user and an optical sensor configured to detect reflected light from which the heart rate reading of the user is determined.

* * * * *